(12) United States Patent
Edwards et al.

(10) Patent No.: US 6,338,726 B1
(45) Date of Patent: *Jan. 15, 2002

(54) TREATING URINARY AND OTHER BODY STRICTURES

(75) Inventors: Stuart D. Edwards, Portola Valley, CA (US); Muta M. Issa, Atlanta, GA (US)

(73) Assignee: Vidacare, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/795,656

(22) Filed: Feb. 6, 1997

(51) Int. Cl.[7] .............................................. A61M 29/00
(52) U.S. Cl. ............................ 604/101.03; 604/103.01; 604/113
(58) Field of Search ........................ 604/96–101, 19–22, 604/51–54, 96.01, 103.01, 101.01, 101.02, 101.03, 113; 606/192, 194, 39, 45, 47; 607/96, 98–102, 138

(56) References Cited

U.S. PATENT DOCUMENTS

| | | | |
|---|---|---|---|
| 4,311,154 A | | 1/1982 | Sterzer et al. |
| 4,674,506 A | * | 6/1987 | Alcond .......................... 604/8 |
| 4,878,492 A | | 11/1989 | Sinofsky et al. |
| 4,955,377 A | | 9/1990 | Lennox et al. |
| 4,994,033 A | | 2/1991 | Shockey et al. |
| 5,007,897 A | | 4/1991 | Kalb et al. |
| 5,049,132 A | | 9/1991 | Shaffer |
| 5,092,841 A | | 3/1992 | Spears |
| 5,100,429 A | * | 3/1992 | Sinofsky et al. ............ 606/195 |
| 5,102,390 A | * | 4/1992 | Crittenden et al. ........... 604/96 |
| 5,188,596 A | | 2/1993 | Condon et al. |
| 5,190,540 A | * | 3/1993 | Lee .............................. 606/28 |
| 5,199,951 A | | 4/1993 | Spears |
| 5,209,776 A | | 5/1993 | Bass et al. |

(List continued on next page.)

FOREIGN PATENT DOCUMENTS

| | | |
|---|---|---|
| WO | WO 92/10142 | 6/1992 |
| WO | WO 95/08289 | 3/1995 |
| WO | WO 97/32532 | 9/1997 |
| WO | WO 98/01087 | 1/1998 |

OTHER PUBLICATIONS

Brian M. Tissue, The Visible Spectrum, Updated Nov. 3, 1996, 2 Pages, Science Hypermedia Home Page.

Marvin J. Slepian, Polymeric Endoluminal Paving and Sealing, 1990, W B Saunders, Philadelphia.

*Primary Examiner*—Anhtuan T. Nguyen
(74) *Attorney, Agent, or Firm*—Micheal A. Glenn; Christopher Peil

(57) ABSTRACT

The invention provides a method and system for treatment of body strictures to restore luminal diameter to within a normal diameter range, in which the stricture is dilated to stretch its lumen to a desired diameter, collagen is exuded near to existing tissue of the stricture so as to be absorbed by that tissue or adhere to that tissue, making a collagen-enhanced tissue structure, and energy is emitted to affect the collagen-enhanced tissue, such as by ablation or by hardening. Ablation and hardening may be repeated so as to create a set of layers of hardened collagen in the form of a supporting frame, preferably having a hollow cylindrical shape. Dilation of the stricture is achieved by expanding one or more balloons, or by the pressure of exuded collagen, until the stricture is larger than a normal diameter range. When energy is emitted into the collagen, the stricture contracts back to the normal diameter range, either by ablation of excess tissue or by plating of the stricture wall. The stricture's tissue is also isolated by a set of balloons at either or both ends of the stricture, so as to isolate the stricture and restrict the collagen to the stricture's tissue. The stricture's tissue is also supported by a stent, which is preferably tackwelded onto the stricture's tissue using collagen. Collagen adheres to the stent, which supports the stricture's tissue until the stent is absorbed into that tissue.

21 Claims, 3 Drawing Sheets

U.S. PATENT DOCUMENTS

| | | |
|---|---|---|
| 5,213,580 A | 5/1993 | Slepian et al. |
| 5,219,355 A | 6/1993 | Parodi et al. |
| 5,257,451 A | 11/1993 | Edwards et al. |
| 5,273,535 A | 12/1993 | Edwards et al. |
| 5,275,162 A | 1/1994 | Edwards et al. |
| 5,278,201 A | 1/1994 | Dunn et al. |
| 5,281,217 A | 1/1994 | Edwards et al. |
| 5,286,254 A | 2/1994 | Shapland et al. |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,318,531 A | 6/1994 | Leone |
| 5,328,467 A | 7/1994 | Edwards et al. |
| 5,328,471 A * | 7/1994 | Slepian ................ 604/101 |
| 5,334,201 A | 8/1994 | Cowan |
| 5,342,357 A | 8/1994 | Nardella |
| 5,363,861 A | 11/1994 | Edwards et al. |
| 5,366,490 A | 11/1994 | Edwards et al. |
| 5,368,592 A | 11/1994 | Stern |
| 5,370,675 A * | 12/1994 | Edwards et al. ........... 607/604 |
| 5,370,678 A | 12/1994 | Edwards et al. |
| 5,383,917 A | 1/1995 | Desai et al. |
| 5,385,544 A | 1/1995 | Edwards et al. |
| 5,398,683 A | 3/1995 | Edwards et al. |
| 5,405,322 A | 4/1995 | Lennox et al. |
| 5,409,453 A | 4/1995 | Lundquist et al. |
| 5,421,819 A | 6/1995 | Edwards et al. |
| 5,423,744 A * | 6/1995 | Gencheff et al. ............ 604/53 |
| 5,423,808 A | 6/1995 | Edwards et al. |
| 5,435,805 A | 7/1995 | Edwards et al. |
| 5,456,662 A | 10/1995 | Edwards et al. |
| 5,456,682 A | 10/1995 | Edwards et al. |
| 5,458,568 A | 10/1995 | Racchini et al. |
| 5,458,596 A | 10/1995 | Lax et al. |
| 5,458,597 A | 10/1995 | Edwards et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,496,271 A | 3/1996 | Burton et al. |
| 5,498,238 A * | 3/1996 | Shapland et al. ............ 604/53 |
| 5,505,730 A | 4/1996 | Edwards et al. |
| 5,507,743 A | 4/1996 | Edwards et al. |
| 5,509,419 A | 4/1996 | Edwards et al. |
| 5,514,131 A | 5/1996 | Edwards et al. |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,542,915 A | 8/1996 | Edwards et al. |
| 5,545,171 A | 8/1996 | Sharkey et al. |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,569,241 A | 10/1996 | Edwards |
| 5,569,242 A | 10/1996 | Lax et al. |
| 5,575,788 A | 11/1996 | Baker et al. |
| 5,582,589 A | 12/1996 | Edwards et al. |
| 5,588,960 A | 12/1996 | Edwards et al. |
| 5,591,125 A | 1/1997 | Edwards et al. |
| 5,591,199 A | 1/1997 | Porter et al. |
| 5,599,294 A | 2/1997 | Edwards et al. |
| 5,599,295 A | 2/1997 | Rosen et al. |
| 5,599,307 A | 2/1997 | Bacher et al. |
| 5,599,345 A | 2/1997 | Edwards et al. |
| 5,599,346 A | 2/1997 | Edwards et al. |
| 5,601,591 A | 2/1997 | Edwards et al. |
| 5,607,389 A | 3/1997 | Edwards et al. |
| 5,624,439 A | 4/1997 | Edwards et al. |
| 5,662,609 A | 9/1997 | Slepian |
| 5,667,488 A | 9/1997 | Lundquist et al. |
| 5,674,191 A | 10/1997 | Edwards et al. |
| 5,681,277 A | 10/1997 | Edwards et al. |
| 5,681,308 A | 10/1997 | Edwards et al. |
| 5,683,384 A | 11/1997 | Gough et al. |
| 5,685,839 A | 11/1997 | Edwards et al. |
| 5,688,266 A | 11/1997 | Edwards et al. |
| 5,707,349 A | 1/1998 | Edwards |
| 5,718,702 A | 2/1998 | Edwards |
| 5,720,718 A | 2/1998 | Rosen |
| 5,720,719 A | 2/1998 | Edwards et al. |
| 5,722,975 A | 3/1998 | Edwards et al. |
| 5,728,094 A | 3/1998 | Edwards |
| 5,728,144 A | 3/1998 | Edwards et al. |
| 5,730,719 A | 3/1998 | Edwards |
| 5,738,114 A | 4/1998 | Edwards |
| 5,741,225 A | 4/1998 | Lax et al. |
| 5,743,870 A | 4/1998 | Edwards |
| 5,743,904 A | 4/1998 | Edwards |
| 5,746,224 A | 5/1998 | Edwards |
| 5,749,846 A | 5/1998 | Edwards et al. |
| 5,762,626 A | 6/1998 | Lundquist et al. |
| 5,769,846 A | 6/1998 | Edwards et al. |
| 5,843,016 A * | 12/1998 | Lugnani et al. ............... 604/21 |

* cited by examiner

TREATING URINARY AND OTHER BODY STRICTURES

BACKGROUND OF THE INVENTION

1. Field of the Invention

This invention relates to techniques for treating urinary strictures.

2. Related Art

A stricture is an abnormally narrowed segment of an otherwise patent biological tube or conduit, such as the gastrointestinal tract, genito-urinary tract, pulmonary system, vascular system, or other systems in the body. Strictures may occur at various places within these systems in the body, such as in or near a blood vessel, the bronchial tree, the colon, a gastrointestinal body structure, a genital body structure, a kidney, a post-operative stricture, a pulmonary body structure, the rectum, or the sphincter, or a urethral body structure. The degree of narrowing, the length, and the significance of the stricture may differ greatly between particular strictures, and is responsive to the nature of the conduit which is subject to the stricture. Various etiological factors might be responsible for the development or exacerbation of any particular stricture; these may include, for example, infection, inflammation, trauma (whether external, internal, or iatrogenic or other surgical trauma), or cancer. One or more of these factors causes the lumen of the affected conduit to narrow, that is, to stricture, with consequential obstruction of the lumen and compromise of the function of the conduit.

Treatment of strictures is aimed at restoration of intraluminal patency and physiological function. Because of the presence of abnormal or diseased tissue at the stricture, surgical treatment by endoscopic or by open surgical techniques often poses extra difficulties and has significant morbidity. Moreover, because the tissue of the stricture wall is already diseased, it often generates further scarring and fibrosis when it heals after surgery, which can lead to recurrence of the stricture.

Accordingly, it would be advantageous to provide a method and system for treatment of strictures, such as for example urinary strictures, which use existing tissue, which promote healing of existing tissue, and which help to prevent recurrence of the stricture. This advantage is achieved in an embodiment of the invention in which a supporting frame, such as a cylindrical collagen frame with a diameter comparable to the normal lumen, is disposed intraluminally in a constricted region of the stricture, energy is emitted to ablate and harden the collagen and the tissue, and the supporting frame is used to maintain patency of the lumen and to prevent reformation of the stricture during a healing period.

SUMMARY OF THE INVENTION

The invention provides a method and system for treatment of body strictures to restore luminal diameter to within a normal diameter range, in which the stricture is dilated to stretch its lumen to a desired diameter, collagen is exuded near to existing tissue of the stricture so as to be absorbed by that tissue or adhere to that tissue, making a collagen-enhanced tissue structure, and energy is emitted to affect the collagen-enhanced tissue, such as by ablation or by hardening. Ablation and hardening may be repeated so as to create a set of layers of hardened collagen in the form of a supporting frame, preferably having a hollow cylindrical shape.

In a preferred embodiment, dilation of the stricture is achieved by expanding one or more balloons, or by the pressure of exuded collagen, until the stricture is larger than a normal diameter range. When energy is emitted into the collagen, the stricture contracts back to the normal diameter range, either by ablation of excess tissue or by plating of the stricture wall.

In a preferred embodiment, the stricture's tissue is also isolated by a set of balloons at either or both ends of the stricture, so as to isolate the stricture and restrict the collagen to the stricture's tissue.

In a preferred embodiment, the stricture's tissue is also supported by a stent, which is preferably tack-welded onto the stricture's tissue using collagen. Collagen adheres to the stent, which supports the stricture's tissue until the stent is absorbed into that tissue.

DETAILED DESCRIPTION OF THE PREFERRED EMBODIMENT

Urinary Stricture

Figure 1:
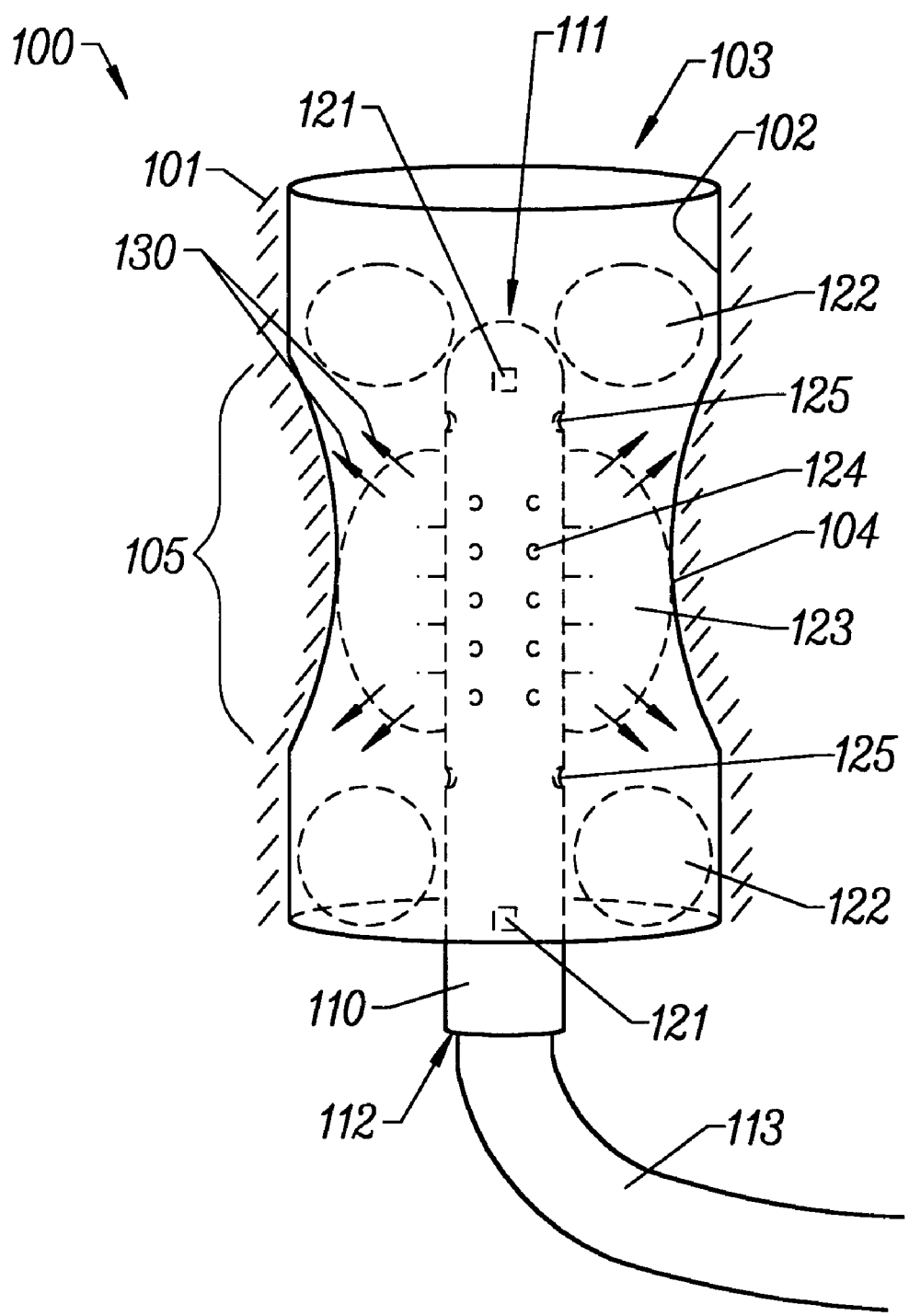
FIG. 1 shows a urinary stricture with a catheter positioned therein.

FIG. 1 shows a urinary stricture with a catheter positioned therein.

A stricture 100 comprises a mass of relatively healthy tissue 101, forming a first portion of a wall 102 for a lumen 103 or other pathway, and a mass of relatively weakened tissue 104, forming a second portion of the wall 102 for the lumen 103 in a constricted region 105. The stricture 100 is shown with the lumen 103 having at least some flow capability, but there are structures 100 in which the flow capability has been reduced to zero, either because the wall 102 in the constricted region 105 has collapsed completely so as to block the lumen 103, because the lumen 103 is blocked with a mass of tissue or other substances (not shown), or some combination of these two problems.

A catheter 110 comprises a distal end 111 and a proximal end 112, the latter being coupled to a tube 113 or other connector for coupling control signals, energy, and fluids between the catheter and 110 and a control system (not shown).

In a preferred embodiment, the catheter 110 comprises a catheter such as shown in one of the following documents or in parent cases thereof: U.S. application Ser. No. 08/717, 612, Express Mail Mailing Number EM266118924US, titled "Ablation of Rectal and Other Internal Body Structures", filed Sep. 20, 1996, attorney docket number VCAR-001, hereby incorporated by reference as if fully set forth herein.

In a preferred embodiment, the cathether 110 is about 5 to about 6 French in width (1 French equals ⅓ of a millimeter or about 0.18 inch). However, in alternative embodiments, the catheter 110 may be of lesser or greater width so as to accomodate strictures of lesser or greater diameter.

The catheter 110 also comprises a first x-ray marker 121, preferably disposed at or near the distal end 111 of the catheter 110 and a second x-ray marker 121, preferably disposed at or near the proximal end 111 of the catheter 110. With suitable x-ray or flouroscopy equipment, a radiologist or surgeon can position the catheter 110 relative to the constricted region 105 without any requirement for a camera or other optical equipment disposed in or near the constricted region 105.

The catheter 110 also comprises a first ring balloon 122, preferably disposed at or near the distal end 111 of the catheter 110 and a ring balloon 122, preferably disposed at or near the proximal end 111 of the catheter 110. The ring balloons 122 are disposed so that, when inflated and in combination with the body of the catheter 110, they physically seal off gas or fluids between the constricted region 105 and other portions of the lumen 103 outside the constricted region 105.

In alternative embodiments, the ring balloons 122 may comprise other shapes, and in particular, the ring balloon 122 disposed at the distal end 111 of the catheter 110 may comprise a spherical or ellipsoidal balloon disposed to seal off the lumen 103 without need for combination with the body of the catheter 110. In such alternative embodiments, the spherical or ellipsoidal balloon is disposed in substantially the same location as shown for the ring balloon 122, except that the spherical or ellipsoidal balloon is disposed to substantially block the lumen 103 and thus seal it off.

In further alternative embodiments, the ring balloons 122 may be porous, microporous, semiporous, or some combination thereof, or may be disposed within the lumen 103 slightly imperfectly, so that so that the seal made by the ring balloons 122 is not necessarily completely gas-tight or even completely fluid-tight.

The catheter 110 also comprises an expansion balloon 123, preferably disposed at or near a middle portion of the catheter 110. The expansion balloon 123 is disposed so that when inflated it physically forces the constricted region 105 of the stricture 100 to open to a greater diameter, such as a diameter within a normal diameter range for the lumen 103.

In a preferred embodiment, the expansion balloon 123 comprises a porous, microporous, or semiporous membrane through which a mass of collagen 130, a solution including saline, or other flowable substances, may flow. The catheter 110 comprises an internal lumen (not shown) which couples flowable substances from the tube 113, so as to exude those flowable substances out from a set of holes 124 and to the expansion balloon 123. When flowable substances are exuded out from the holes 124 to the expansion balloon 123, pressure from the flowable substances causes the expansion balloon 123 to expand and to physically force the constricted region 105 of the stricture 100 to open to the greater diameter.

In a preferred embodiment, the expansion balloon 123 comprises a spherical or ellipsoidal shape, so as to expand in a middle region near the stricture 105. In a preferred method of operation, the expansion balloon 123 is first expanded to its maximum diameter, then deflated somewhat so as to allow flowable substances to flow into the region of the stricture 105.

However, in alternative embodiments, the expansion balloon 123 may comprise another shape, such as a concave shape (shaped somewhat like the stricture itself) having a greater degree of expansion at a distal end of the stricture 105 and at a proximal end of the stricture 105, and having a lesser degree of expansion at a middle portion of the stricture 105. The expansion balloon 123 can take on this concave shape by being comprised of a relatively thinner (and therefore more expansible) rubber material at the distal end of the stricture 105 and at the proximal end of the stricture 105, while being comprised of a relatively thicker (and therfore less expansible) rubber material at the middle portion of the stricture 105.

The catheter 110 also comprises a set of electrodes 125, preferably disposed at or near a middle portion of the catheter 110. The electrodes 125 are coupled using the tube 113 to a power source (not shown). The power source provides energy to the electrodes 125, which emit that energy into the constricted region 105 of the stricture 100 so as to affect the mass of collagen 130, the relatively weakened tissue 104, and (in some embodiments) the relatively healthy tissue 101.

The catheter 110 also comprises a set of sensors 126, preferably disposed at or near a surface of the catheter 110. The sensors 126 are coupled using the tube 113 to a control system (not shown) and to an operator display (not shown). The sensors 126 provide signals to the control system for feedback control, and to the operator display for displaying information to an operator.

In a preferred embodiment, the sensors 126 comprise a plurality of temperature sensors, such as thermistors or thermocouples, and the control system provides feedback control to maintain a temperature of the mass of collagen 130 at a temperature selected by the operator. In a preferred embodiment, the operator display comprises a temperature reporting gauge. However, it would be clear to those skilled in the art that other and further sensor signals, feedback control, and display signals, would be useful, and are within the scope and spirit of the invention.

Method of Operation

Figure 2:
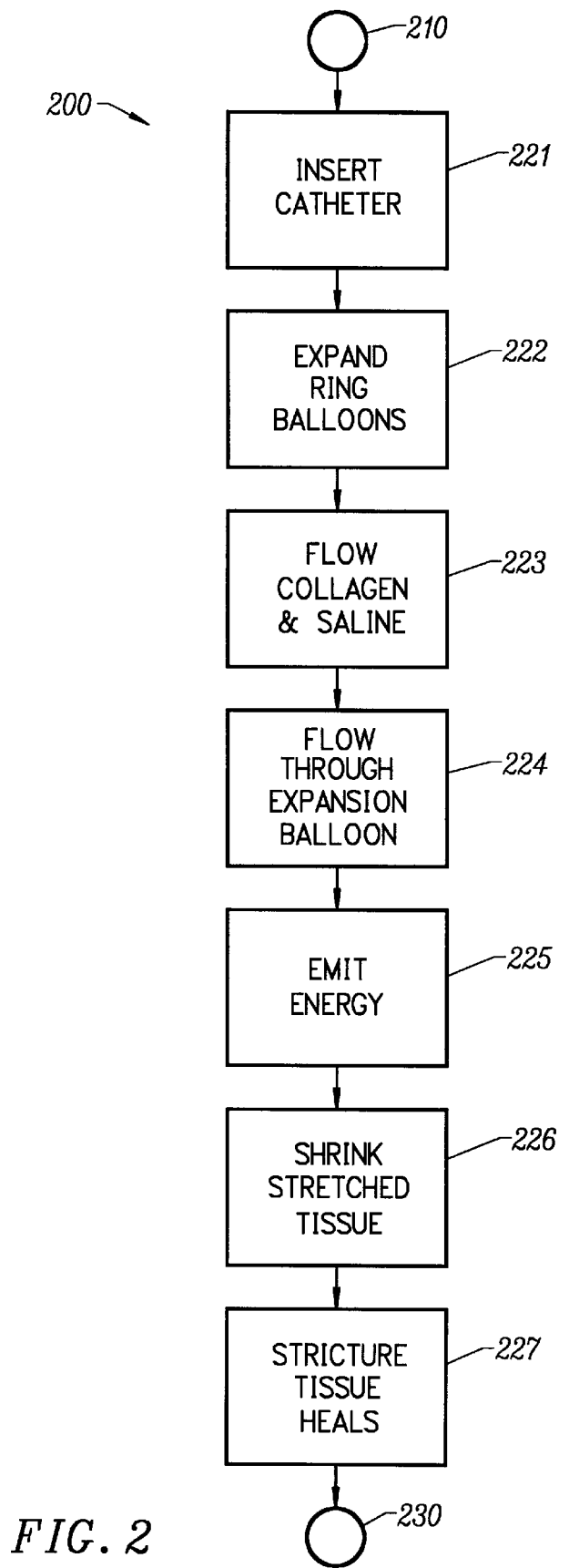
FIG. 2 is a flowchart for a method of operation for the catheter.

FIG. 2 is a flowchart for a method of operation for the catheter.

A method 200 of operation for the catheter 110 comprises a sequence of steps between the flow points 210 and 230. In a preferred embodiment, the method 200 is carried out using the catheter 110, as well as other and further equipment which would be clearly deemed necessary or desirable by those skilled in the art.

At a flow point 210, it is desired to treat the urinary stricture 100.

At a step 221, the catheter 110 is inserted into the constricted region 105 of the urinary stricture 100. As noted herein, the radiologist or surgeon positions the catheter 110 relative to the urinary stricture 100 using the x-ray markers 121 and an flouroscope or other x-ray device.

At a step 222, the first ring balloon 122 and the second ring balloon 122 are expanded to isolate the constricted region 105 from other portions of the lumen 103 in a gas-tight and fluid-tight manner.

At a step 223, the mass of collagen 130 and a saline solution are flowed through the tube 113, through the body of the catheter 110, through the holes 124, and into the expansion balloon 123. The flow of the mass of collagen 130 and the saline solution into the expansion balloon 123 causes the expansion balloon 123 to expand, physically forcing the relatively weakened tissue 104 out to a diameter greater than the normal diameter range for the lumen 103.

At a step 224, the mass of collagen 130 and the saline solution are flowed through the expansion balloon 123, into contact with the relatively weakened tissue 104. The mass of collagen 130 and the saline solution are absorbed into the relatively weakened tissue 104.

At a step 225, electrical energy is conducted from the power source through the tube 113, through the body of the catheter 110, to the electrodes 125. The electrodes 125 emit RF energy (at a preferred frequency of between about 400 megahertz and about 700 megahertz, but possibly at other frequencies, such as micro wave frequencies), which is received by the saline solution and thus transmitted to the relatively weakened tissue 104.

The relatively weakened tissue 104, having been suffused with the mass of collagen 130, receives the RF energy emitted by the electrodes 125 and is ablated. As RF energy is received by the relatively weakened tissue 104, the relatively weakened tissue 104 is heated to at least about 90 to 120 degrees Celsuius, causing ablation to occur by means of cell death, dehydration, denaturation, or other means.

In a second preferred embodiment, the mass of collagen 130 forms a surface layer over the of the wall 102 of the relatively weakened tissue 104. At the step 224, the mass of collagen 130 adheres to the surface while the saline solution is absorbed into the relatively weakened tissue 104. At the step 225, the mass of collagen 130 is cooked or otherwise thermoset by the RF energy so as to solidify into a layer of hardened collagen, preferably about 1 mil (0.001 inch or about 0.0025 centimeters) in thickness. The step 224 and the step 225 are repeated a number of times sufficient to create a layer of hardened collagen effective to restrain fluid flowing in the lumen 103 from seeping into the relatively weakened tissue 104.

The mass of collagen 130, having been heated by application of RF energy, cooks or otherwise thermosets to a solidified state.

At a step 226, the relatively weakened tissue 104, having been ablated, shrinks to a diameter within a normal diameter range for the lumen 103.

At a step 227, the relatively weakened tissue 104, as supported by the mass of collagen 130, is allowed to heal by growth of epithelial cells.

At a flow point 230, the urinary stricture 100 has been treated and should be in condition for normal operation.

In alternative embodiments, the method 200 may be applied to other body structures or other places within the gastrointestinal tract, genito-urinary tract, pulmonary system, vascular system, or other systems in the body, such as in or near a blood vessel, the bronchial tree, the colon, a gastrointestinal body structure, a genital body structure, a kidney, a postoperative stricture, a pulmonary body structure, the rectum, the sphincter, or a urethral body structure.

Figure 3:
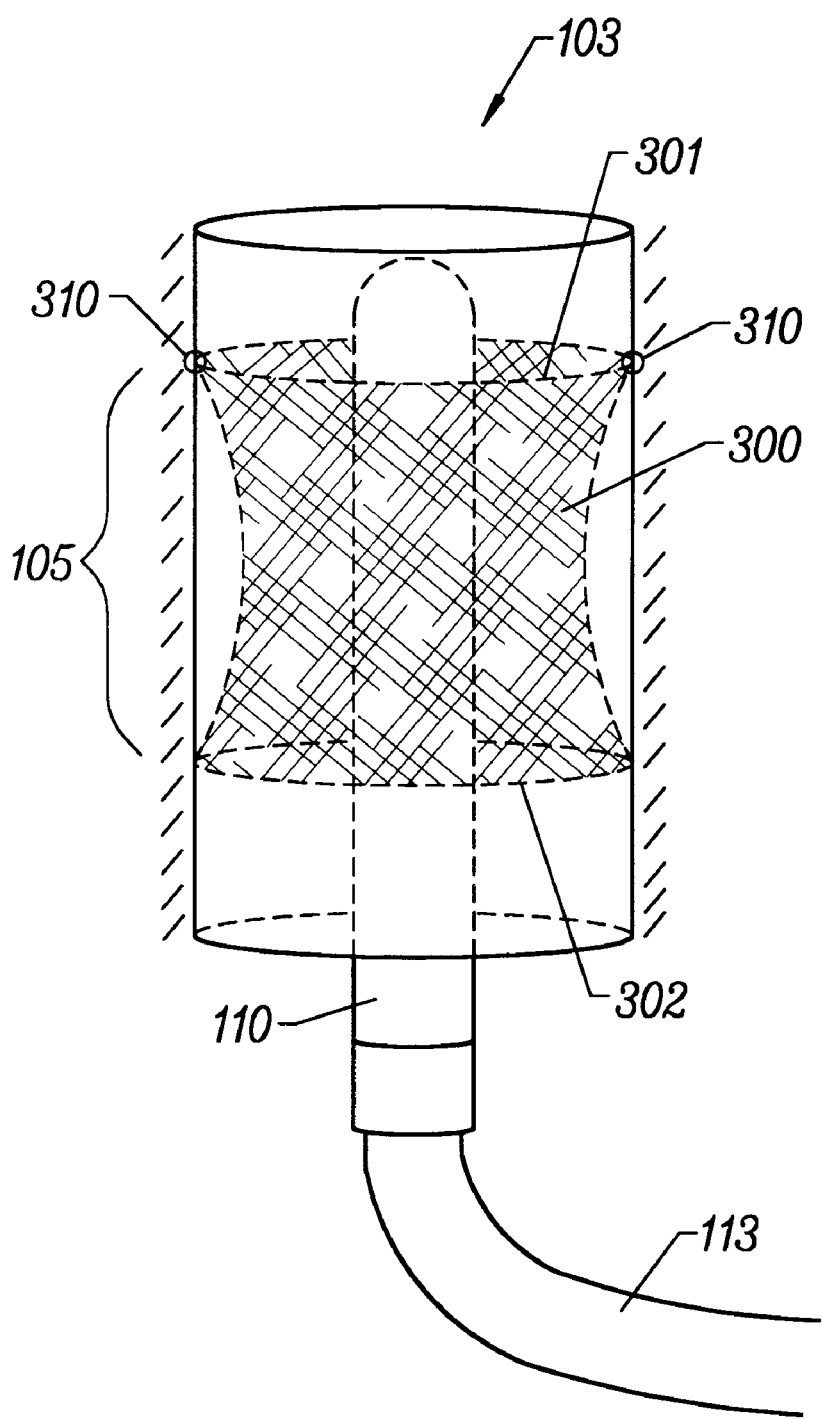
FIG. 3 shows a urinary stricture with a stent positioned and attached therein.

FIG. 3 shows a urinary stricture with a stent positioned and attached therein.

A stent 300 comprises a substantially cylindrical structure having a distal end 301 and a proximal end 302, and formed in the shape of a mesh or a woven structure, such as used in gauze or stretchable fabrics. In a preferred embodiment, the stent 300 comprises a suture material, such as catgut, polygalactic polymer 910, or PDS.

The stent 300 is disposed in the urinary stricture 100 by coupling the stent 300 to the catheter 110, disposing the catheter 110 substantially within the constricted region 105 of the urinary stricture 100, and coupling the stent 300 to at least a portion of the urinary stricture 100.

The stent 300 is coupled to the urinary stricture 100 by coupling the distal end 301 of the stent 300 to a coupling spot 310 on the relatively healty tissue 101 outside the constricted region 105 of the urinary stricture 100 by means of "tack welding". "Tack welding" refers to disposing the distal end 301 of the stent 300 at the coupling spot 310, exuding collagen so as to adhere to both the distal end 301 of the stent 300 and the coupling spot 310, and emitting energy so as to harden the collagen to permanently or semipermanently couple the distal end 301 of the stent 300 to the coupling spot 310.

In a preferred embodiment, the coupling spot 310 comprises a O-shaped ring around the lumen 103.

Alternative embodiments

Although preferred embodiments are disclosed herein, many variations are possible which remain within the concept, scope, and spirit of the invention, and these variations would become clear to those skilled in the art after perusal of this application.

What is claimed is:

1. Apparatus for treatment of a stricture within the body, said apparatus including:

a multi-lumen catheter having a proximal end and a distal end:

a radiology marker located in distal end of said catheter:

a first inflatable balloon located at distal end of said catheter and a second inflatable balloon located at proximal end of said catheter, both first and second balloons being connected to a source of substantially non-translucent inflation fluid by a lumen running longitudinally through said catheter, wherein at least said first balloon is any of a ring, an ellipsoid and a spherical balloon, and wherein at least said first balloon need not be combined with body of said catheter, at least one of said first and second balloons when inflated by said inflation fluid being effective to stabilize a position of said catheter during said treatment and achieve at least one seal against a surface of said stricture, wherein said seal is at least partially gas-tight and at least partially fluid-tight, thereby confining at least a portion of said stricture between said first and second balloons;

at least one first port located on surface of said catheter between said first and second balloons, said first port being connected with a source of substantially non-translucent treatment by a lumen running longitudinally through said catheter and disposed to exude a first mass of said treatment fluid into said confined portion of said stricture under a first pressure and for a first time, said first pressure and said first time being effective to dilate said structure and cause at least a portion of said first mass of treatment fluid to be suffused into at least a portion of an existing tissue of said confined portion of said stricture;

at least one temperature sensor on the surface of said catheter, said temperature sensor being connected to a control system by a lumen running longitudinally through said catheter;

at least one electrode included in said catheter and coupled to said conductor, said electrode being adapted to emit energy and raise a temperature, substantially proximate to said catheter only, to at least 100 degrees Celsius, for a time effective to couple at least a portion of said suffused and absorbed treatment fluid with at least a portion of said mass of existing tissue into a unified tissue matrix.

2. Apparatus as in claim 1, wherein said seal is at least one of the following: fluid-tight, gas-tight, or both fluid-tight and gas-tight.

3. Apparatus as in claim 1, wherein said energy is at least one of the following: RF energy in a frequency range of approximately 450 to 600 MHz, microwave energy, pulsed wave form energy.

4. Apparatus as in claim 1, wherein said treatment fluid is at least one of the following: a collagenous fluid, a bioactive fluid, a chemoactive fluid.

5. Apparatus as in claim 1, wherein said electrode emits an amount of said energy effective to harden at least a portion of said unified tissue matrix.

6. Apparatus as in claim 1, wherein said electrode emits an amount of said energy effective to ablate, substantially proximate to said catheter only, at least a portion of said mass of confined existing tissue of said stricture.

7. Apparatus as in claim 1, wherein said electrode emits an amount of said energy effective to ablate, substantially proximate to said catheter housing only, at least a portion of said unified tissue matrix.

8. Apparatus as in claim 1, wherein said electrode emits an amount of said energy effective to ablate, substantially proximate to said catheter only, at least a portion of said unified tissue matrix and cause it to contract from said dilatated condition to within a normal diameter range for said stricture.

9. Apparatus as in claim 1, wherein said first and second balloons are connected to separate sources of substantially non-translucent inflation fluid by separate lumina running longitudinally through said catheter, such that said first and second balloons can be separately inflated under different pressures and/or to different diameters.

10. Apparatus as in claim 1, including at least one second port located on the surface of said catheter housing between said first and second balloons and connected to a lumen running longitudinally through said catheter, said second port being effective to flush and evacuate from said confined portion of said stricture at least one of the following: a bodily fluid, said treatment fluid, said collagenous fluid, said bioactive fluid, said chemoactive fluid, or a detritus resulting from ablation.

11. Apparatus as in claim 10, including a third inflatable balloon located on said electrode housing between said first and second balloons such that said third balloon envelops said first port but does not envelope said second port, said third balloon being inflated by said pressure of said treatment fluid through said first port.

12. Apparatus as in claim 1, wherein said third inflatable balloon includes at least one of the following: a semi-porous membrane, a porous membrane, a microporous membrane, or a combination of semi-porous, porous and/or microporous membranes.

13. Apparatus as in claim 1, wherein
    said first port is effective to exude a second mass of said substantially non-translucent treatment fluid into said confined portion of said stricture under a second pressure and for a second time, said second pressure and said second time being effective to cause at least a portion of said second mass of exuded treatment fluid to create a layer about one (1) mil in thickness on an inner surface of said stricture;
    said electrode emits an amount of said energy effective to couple at least a portion of said layer to at least a portion of said inner surface.

14. Apparatus as in claim 13, wherein said electrode emits an amount of said energy effective to harden at least a portion of said layer.

15. Apparatus as in claim 13, including means effective to create multiple layers of said treatment fluid.

16. Apparatus as in claim 13, wherein said electrode emits an amount of said energy effective to ablate, substantially proximate to said electrode housing only, at least a portion of said layer.

17. Apparatus as in claim 1, including
    a stent;
    means for inserting said stent into said stricture whereby said stent is operative to retard collapse of said stricture.

18. Apparatus as in claim 16, wherein said stent includes at least one of the following substances: collagen, catgut, polyglactin 910, or PDS.

19. Apparatus as in claim 16, wherein said stent includes at least one end, and wherein said first port and said ring electrode are effective to anchor said end of said stent to an existing tissue adjacent to said stricture.

20. Apparatus for treatment of a stricture within the body, said apparatus including:
    a multi-lumen catheter having a proximal end and a distal end:
    a radiology marker located in distal end of said catheter:
    a first inflatable balloon located at distal end of said catheter and a second inflatable balloon located at proximal end of said catheter, both first and second balloons being connected to a source of substantially non-translucent inflation fluid by a lumen running longitudinally through said catheter, wherein at least said first balloon is any of a ring, an ellipsoid and a spherical balloon, and wherein at least said first balloon need not be combined with body of said catheter, at least one of said first and second balloons when inflated by said inflation fluid being effective to stabilize a position of said catheter during said treatment and achieve at least one seal against a surface of said stricture, wherein said seal is at least partially gas-tight and/or at least partially fluid-tight, thereby confining at least a portion of said stricture between said first and second balloons;
    at least one first port located on surface of said catheter between said first and second balloons, said first port being connected with a source of substantially non-translucent treatment fluid by a lumen running longitudinally through said catheter and disposed to exude a first mass of said treatment fluid into said confined portion of said stricture under a first pressure and for a first time, said first pressure and said first time being effective to dilate said structure and cause at least a portion of said first mass of treatment fluid to be suffused into at least a portion of an existing tissue of said confined portion of said stricture;
    a third inflatable balloon located on said catheter between said first and second balloons such that said third balloon envelops said first port, said third balloon being inflated by said pressure of said treatment fluid through said first port, wherein said third balloon includes at least one of the following; a semi-porous membrane, or a combination of semi-porous, porous and micro-membranes;
    at least one temperature sensor on the surface of said catheter, said temperature sensor being connected to a control system by a lumen running longitudinally through said catheter;
    at least one electrode included in said catheter and coupled to said conductor, said electrode being adapted to emit energy and raise a temperature, substantially proximate to said catheter only, to at least 100 degrees Celsius, for a time effective to couple at least a portion of said suffused and absorbed treatment fluid with at least a portion of said mass of existing tissue into a unified tissue matrix.

21. A method for treatment of a stricture within a region of the body, said stricture comprising a lumen in said body region being constricted smaller than a normal diameter range, comprising the steps of:
    inserting a multi-lumen catheter into said body region;
    stabilizing position of said catheter during said treatment by means of a first inflatable balloon located at distal end of said catheter and a second inflatable balloon located at proximal end of said catheter, both first and second balloons being connected to a source of substantially non-translucent inflation fluid by a lumen running longitudinally through said catheter, wherein at least said first balloon is one of a ring, an ellipsoid and a spherical balloon, and wherein at least said first balloon need not be combined with body of said catheter, at least one of said first and second balloons when inflated by said inflation fluid being effective to achieve at least one seal against a surface of said stricture, wherein said seal is at least partially gas-tight and at least partially fluid-tight, so that at least a portion of said stricture is confined between said first and second balloons;

dilating said stricture, wherein dilating comprises one or both of:

exuding a first mass of substantially non-translucent treatment fluid from a port located on surface of said catheter between said first and second balloons, said port being connected with a source of said treatment fluid by a lumen running longitudinally through said catheter and disposed into said confined portion of said stricture under a first pressure and for a first time, said first pressure and said first time being effective to dilate said stricture; and inflating a third inflatable balloon, said third balloon located on said catheter between said first and second balloons such that said third balloon envelops said port, so that said third balloon is inflated by said pressure of said treatment fluid through said port, said third balloon including at least one of: a porous membrane, a microporous membrane, and a combination of semi-porous, porous and/or microporous membranes, wherein said treatment fluid is exuded by said membrane;

wherein at least a portion of said first mass of treatment fluid is suffused and absorbed into at least a portion of an existing tissue of said confined portion of said stricture; and coupling at least a portion of said suffused and absorbed treatment fluid with at least a portion of said mass of existing tissue by emitting energy from an electrode included in said catheter, said electrode being adapted to emit energy and raise temperature, substantially proximate to said catheter only, to at least 100 degrees Celsius, for a time effective to couple said treatment fluid with said tissue mass.

\* \* \* \* \*